(12) United States Patent
Pascal

(10) Patent No.: US 8,987,484 B2
(45) Date of Patent: Mar. 24, 2015

(54) PROCESS FOR THE PRODUCTION OF ESTETROL

(71) Applicant: Estetra S.P.R.L., Bierset (BE)

(72) Inventor: Jean-Claude Pascal, Nice (FR)

(73) Assignee: Estetra S.P.R.L., Bierset (BE)

( * ) Notice: Subject to any disclaimer, the term of this patent is extended or adjusted under 35 U.S.C. 154(b) by 0 days.

(21) Appl. No.: 14/349,940

(22) PCT Filed: Oct. 5, 2012

(86) PCT No.: PCT/EP2012/069761
§ 371 (c)(1),
(2) Date: Apr. 4, 2014

(87) PCT Pub. No.: WO2013/050553
PCT Pub. Date: Apr. 11, 2013

(65) Prior Publication Data
US 2014/0243539 A1   Aug. 28, 2014

Related U.S. Application Data

(60) Provisional application No. 61/544,591, filed on Oct. 7, 2011.

(30) Foreign Application Priority Data

Oct. 7, 2011   (EP) ................................ 11184278

(51) Int. Cl.
*C07J 75/00*   (2006.01)
*C07J 1/00*   (2006.01)

(52) U.S. Cl.
CPC ............. *C07J 1/0066* (2013.01); *C07J 75/00* (2013.01)
USPC ........................................................ 552/617

(58) Field of Classification Search
CPC ...................................................... C07J 75/00
See application file for complete search history.

(56) References Cited

FOREIGN PATENT DOCUMENTS

| NL | 2383279 A1 * | 11/2011 |
| WO | WO-2004/041839 A2 | 5/2004 |
| WO | WO-2012/164095 A1 | 12/2012 |
| WO | WO-2012/164096 A1 | 12/2012 |

OTHER PUBLICATIONS

Greene, Protective Groups in Organic Chemistry, 1981, John Wiley & Sons, New York, pp. 44-46 and 53-55.*
Fishman, J. et al., "Synthesis of Epimeric 15-Hydroxyestriols, New and Potential Metabolites of Estradiol," J. Org. Chem., 33(8):3133-3135 (1968).
Warmerdam, E.G.J.C. et al., "A New Route of Synthesis of Estetrol," Climacteric, 11:59-63 (2008).
International Search Report dated Dec. 12, 2012 for PCT/EP2012/069761.
Larock et al, A Simple, Effective, New, Palladium-Catalyzed Conversion of Enol Silanes to Enones and Enals:, Tetrahedron Letters, vol. 36, No. 14, pp. 2423-2426 (1995).
Trost et al., "Methyl 2-Pyridinesulfinate. A Convenient Reagent for Sulfinylation-Dehydrosulfinylation", Journal Organic Chemistry, vol. 58, pp. 1579-1581 (1993).

* cited by examiner

*Primary Examiner* — Paul A Zucker
(74) *Attorney, Agent, or Firm* — Foley Hong LLP; David P. Halstead

(57) ABSTRACT

The present invention relates to a process for the preparation of a compound of formula (I), hydrates or solvates thereof.

15 Claims, No Drawings

PROCESS FOR THE PRODUCTION OF ESTETROL

This application is a national-stage application under 35 U.S.C. §371 based on Patent Cooperation Treaty Application serial number PCT/EP2012/069761, filed Oct. 5, 2012, which claims the benefit of priority to EP 11184278.7, filed on Oct. 7, 2011, and U.S. Provisional Patent Application Ser. No. 61/544,591, filed on Oct. 7, 2011.

FIELD OF THE INVENTION

The present invention relates to a new process for the synthesis of Estetrol.

BACKGROUND OF THE INVENTION

Estrogenic substances are commonly used in methods of Hormone Replacement Therapy (HRT) and methods of female contraception. Estetrol is a biogenic estrogen that is endogenously produced by the fetal liver during human pregnancy. Recently, estetrol has been found effective as an estrogenic substance for use in HRT. Other important applications of estetrol are in the fields of contraception, therapy of autoimmune diseases, prevention and therapy of breast and colon tumors, enhancement of libido, skin care, and wound healing.

The synthesis of estetrol and derivatives thereof is known in the art. J. FISHMAN and H. GUZIK (J. Org. Chem, Vol 33, No 8, 3133-3135, 1968) describe a route to estra-1,3,5(10)-triene-3,15α,16α,17β-tetrol (estetrol) involving cis hydroxylation of the double bond of an α-β-unsaturated dioxolane derivative of formula A, wherein Ac is acetyl.

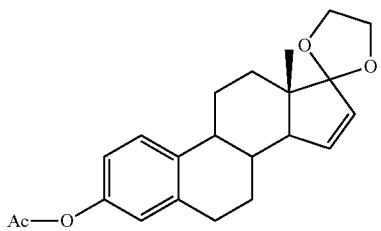

(A)

Osmium tetraoxyde was used for the cis hydroxylation of compound (A) and gave the 17,17-ethylenedioxyestra-1,3,5(10)-triene-3,15α,16α-triol 3-acetate as the major product. However attempts to remove the dioxolane group failed completely.

The carbonyl group at $C_{17}$ of the 3-hydroxyestetra-1,3,5(10),15-tetraen-17-one was reduced with $LiAlH_4$ to estra-1,3,5(10),15-tetraene-3,17-diol that was isolated as the diacetate (compound B). Compound B was subjected to cis-hydroxylation of the double bond of D ring by using Osmium tetraoxyde which resulted into the formation of estra-1,3,5(10)-triene-3,15α,16α,17α-tetraol-3,17-diacetate (compound C) as the major product associated with estra-1,3,5(10)-triene-3,15β,16β,17β-tetrol-3,17 diacetate. These compounds were isolated by thin layer chromatography. Compound C under heating with $K_2CO_3$ in methanol produces estetrol (compound D) (Scheme 1). The overall yield of this three step process was, starting from estrone 3-hydroxyestetra-1,3,5(10),15-tetraen-17-one, only about 7%.

Scheme 1

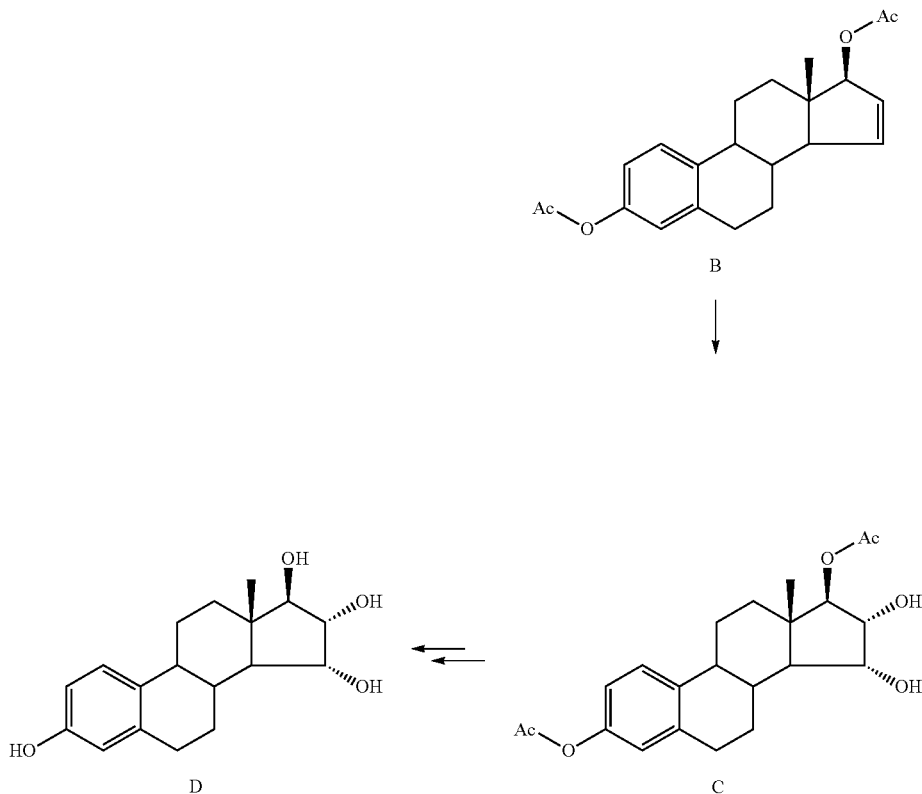

Verhaar M. T; et al (WO 2004/041839) describes a process for the preparation of estetrol by cis hydroxylation of 17-acetyloxy-3-benzyloxy-estra-1,3,5(10),15-tetraene using osmium tetraoxyde and trimethyl-amine N-oxide in THF at 50° C. The resulting 15,16-dihydroxylated crude derivative was obtained in 84% yield but several crystallizations were needed in order to purify this intermediate. Finally the yield after these purifications was about 43%.

Bull, James R; et al in Journal of the Chemical Society, Perkin Transactions 1: Organic and Bio-Organic Chemistry (1972-1999), (2), 241-51; 1990 described cis hydroxylation using osmium tetraoxyde on a 14,17-ethano derivative of formula (E) wherein Pa is a methyl group and Pb is an acetyl group. A mixture was obtained consisting of about 56% of the α,α-dihydroxy and 27% of the β,β-dihydroxy derivative.

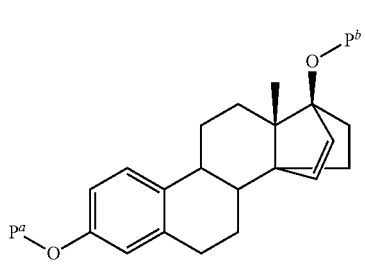

(E)

Beside the poor selectivity for osmium-catalyzed dihydroxylation of these 17β-acetyloxy derivatives, exhaustive purifications are needed.

There remain a need for an improved synthesis of estra-1, 3,5 (10),15α,16α,17β-tetrol (estetrol).

It is therefore an object of the present invention to provide a process for the preparation of estra-1,3,5(10)-triene 15α, 16α,17β-tetrol which overcome at least one the disadvantages of the prior art.

SUMMARY OF THE INVENTION

The present inventors have now found that this object can be obtained by using a process as defined in the appended claims.

According to the present invention, a process for the preparation of a compound of formula (I) (estra-1,3,5(10)-triene-3,15α,16α,17β-tetrol) is provided:

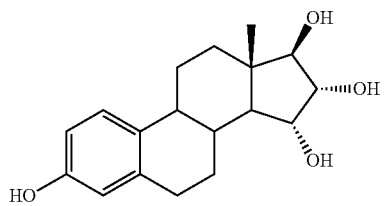

(I)

said process comprises the steps of:

a) reacting a compound of formula (II), with an acylating or a silylating agent to produce a compound of formula (III),

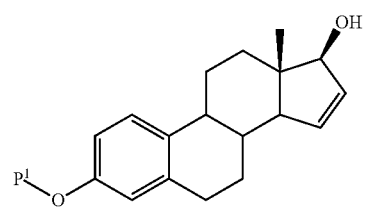

(II)

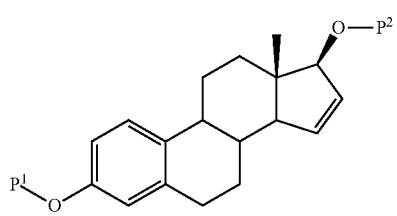

(III)

wherein $P^1$ is a protecting group selected from $R^1CO-$, or $R^2Si(R^3)(R^4)-$, $P^2$ is a protecting group selected from $(R^6R^5R^7)C-CO-$, or $(R^2)Si(R^3)(R^4)-$, wherein $R^1$ is a group selected from $C_{1-6}$alkyl or $C_{3-6}$cycloalkyl, each group being optionally substituted by one or more substituents independently selected from fluoro or $C_{1-4}$alkyl; $R^2$, $R^3$ and $R^4$ are each independently a group selected from $C_{1-6}$alkyl or phenyl, each group being optionally substituted by one or more substituents independently selected from fluoro or $C_{1-4}$alkyl; $R^5$ is a group selected from $C_{1-6}$alkyl or phenyl, each group being optionally substituted by one or more substituents independently selected from fluoro or $C_{1-4}$alkyl; $R^6$ and $R^7$ are each independently hydrogen or a group selected from $C_{1-6}$alkyl or phenyl, each group being optionally substituted by one or more substituents independently selected from fluoro or $C_{1-4}$alkyl;

b) reacting the compound of formula (III) in the presence of at least one oxidizing agent selected from permanganate salt, osmium oxide, hydrogen peroxide, or iodine and silver acetate to produce compound of formula (IV); and

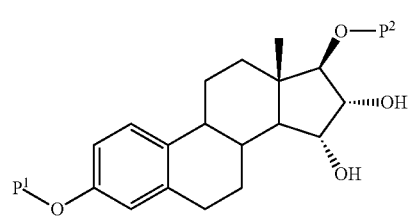

(IV)

c) deprotecting the compound of formula (IV) to produce compound of formula (I).

The invention provides an improved process for producing a compound of formula (I) in significantly higher yield and for at lower cost than possible by the previous known syntheses. In particular, the present process allows the preparation of estra-1,3,5(10)-triene-3,15α,16α,17β-tetrol as the major product with little or no estra-1,3,5(10)-triene-3,15β,16β, 17β-tetrol isomer.

According to a second aspect, the present invention also encompasses estetrol directly obtained by the process according to the present invention, for use in a method selected from a method of hormone replacement therapy, a method of treating vaginal dryness, a method of contraception, a method of enhancing libido, of method of treating skin, a method of promoting wound healing, and a method of treating or preventing a disorder selected from the group consisting of autoimmune diseases, breast tumors and colorectal tumors.

The above and other characteristics, features and advantages of the present invention will become apparent from the following detailed description, which illustrate, by way of example, the principles of the invention.

DETAILED DESCRIPTION OF THE INVENTION

It is also to be understood that the terminology used herein is not intended to be limiting, since the scope of the present invention will be limited only by the appended claims.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. It will be appreciated that the terms "comprising", "comprises" and "comprised of" as used herein comprise the terms "consisting of", "consists" and "consists of".

The recitation of numerical ranges by endpoints includes all numbers and fractions subsumed within the respective ranges, as well as the recited endpoints.

All references cited in the present specification are hereby incorporated by reference in their entirety. In particular, the teachings of all references herein specifically referred to are incorporated by reference.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the appended claims, any of the claimed embodiments can be used in any combination.

The term "alkyl" by itself or as part of another substituent, refers to a straight or branched saturated hydrocarbon group joined by single carbon-carbon bonds having 1 to 6 carbon atoms, for example 1 to 5 carbon atoms, for example 1 to 4 carbon atoms, preferably 1 to 3 carbon atoms. When a subscript is used herein following a carbon atom, the subscript refers to the number of carbon atoms that the named group may contain. Thus, for example, $C_{1-6}$alkyl means an alkyl of one to six carbon atoms. Examples of alkyl groups are methyl, ethyl, propyl, isopropyl, butyl, isobutyl, sec-butyl, tert-butyl, 2-methylbutyl, pentyl iso-amyl and its isomers, hexyl and its isomers.

The term "$C_{3-6}$cycloalkyl", as a group or part of a group, refers to a saturated or partially saturated cyclic alkyl radical containing from about 3 to about 6 carbon atoms. Examples of monocyclic $C_{3-6}$cycloalkyl radicals include cyclopropyl, cyclobutyl, cyclopentyl, or cyclohexyl.

The term "$C_{2-6}$alkenyl" by itself or as part of another substituent, refers to an unsaturated hydrocarbyl group, which may be linear, or branched, comprising one or more carbon-carbon double bonds. Examples of $C_{2-6}$alkenyl groups are ethenyl, 2-propenyl, 2-butenyl, 3-butenyl, 2-pentenyl and its isomers, 2-hexenyl and its isomers, 2,4-pentadienyl and the like.

The term "$C_{6-10}$aryl", by itself or as part of another substituent, as a group or part of a group, refers to a polyunsaturated, aromatic hydrocarbyl group having a single ring (i.e. phenyl) or multiple rings fused together (e.g. naphthalene), or linked covalently, typically containing 6 to 10 atoms; wherein at least one ring is aromatic. Non-limiting examples of $C_{6-10}$aryl include phenyl ($C_6$aryl), naphthyl, indanyl, or 1,2,3,4-tetrahydro-naphthyl.

The term "$C_{1-6}$alkylcarbonyl", as a group or part of a group, represents a group of Formula —CO—$R^a$, wherein $R^a$ is $C_{1-6}$alkyl as defined herein.

The term "$C_{3-6}$cycloalkylcarbonyl", as a group or part of a group, represents a group of Formula —CO—$R^c$, wherein $R^a$ is $C_{3-6}$cycloalkyl as defined herein.

The term "$C_{2-6}$alkenyl$C_{1-6}$alkanoate" refers to a compound having the Formula $R^b$—O—CO—$R^a$ wherein $R^a$ is $C_{1-6}$alkyl as defined herein and $R^b$ is $C_{2-6}$alkenyl as defined herein.

The term "$C_{2-6}$alkenyl$C_{3-6}$cycloalkanoate" refers to a compound having the Formula $R^b$—O—CO—$R^c$ wherein $R^c$ is $C_{3-6}$cycloalkyl as defined herein and $R^b$ is $C_{2-6}$alkenyl as defined herein.

The term "$C_{1-6}$alkylenecarbonate" refers to a compound having the Formula $R^b$—O—CO—O—$R^a$ wherein $R^a$ is $C_{1-6}$alkyl as defined herein and $R^b$ is $C_{2-6}$alkenyl as defined herein.

The term "heteroaryl", by itself or as part of another substituent, refers to an aromatic monocyclic or polycyclic heterocycle having preferably 5 to 7 ring atoms and more preferably 5 to 6 ring atoms, which contains one or more heteroatom ring members selected from nitrogen, oxygen or sulfur. Non-limiting examples of a heteroaryl include: pyridinyl, pyrrolyl, furanyl, thiophenyl, pyrazolyl, imidazolyl, oxazolyl, isoxazolyl, thiazolyl, isothiazolyl, triazolyl, oxadiazolyl, thiadiazolyl, tetrazolyl, oxatriazolyl, thiatriazolyl, pyrimidyl, pyrazinyl, pyridazinyl, oxazinyl, dioxinyl, thiazinyl, triazinyl. Preferably heteroaryl is selected from the group comprising pyridinyl, pyrrolyl, furanyl, thiophenyl, imidazolyl, pyrazolyl, oxazolyl, thiazolyl, and pyrazinyl. More preferably heteroaryl is pyridinyl.

The present invention relates to a process for preparing compound of formula (I); wherein said process comprises the steps of a) reacting a compound of formula (II), with an acylating or a silylating agent to produce a compound of formula (III),

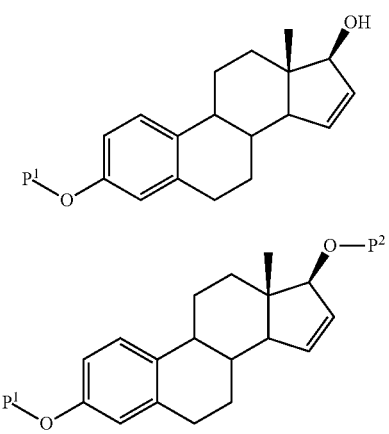

(II)

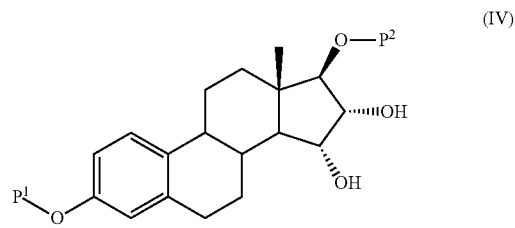

(III)

wherein

P$^1$ is a protecting group selected from R$^1$CO—, or R$^2$Si(R$^3$)(R$^4$)—,

P$^2$ is a protecting group selected from (R$^6$R$^5$R$^7$)C—CO—, or (R$^2$)Si(R$^3$)(R$^4$)—, R$^1$ is a group selected from C$_{1-6}$alkyl or C$_{3-6}$cycloalkyl, each group being optionally substituted by 1, 2 or 3 substituents independently selected from fluoro or C$_{1-4}$alkyl; preferably R$^1$ is selected from the group comprising methyl, ethyl, propyl, isopropyl, butyl, isobutyl, tert-butyl, cyclopropyl, cyclobutyl, cyclopentyl, or cyclohexyl, each group being optionally substituted by 1, 2 or 3 substituents independently selected from fluoro or C$_{1-4}$alkyl; more preferably R$^1$ is methyl, ethyl, propyl, isopropyl, cyclopentyl, or cyclohexyl, yet more preferably R$^1$ is methyl, or ethyl;

R$^2$, R$^3$ and R$^4$ are each independently a group selected from C$_{1-6}$alkyl or phenyl, each group being optionally substituted by one or more substituents independently selected from fluoro or C$_{1-4}$alkyl; preferably R$^2$, R$^3$ and R$^4$ are each independently selected from the group comprising methyl, ethyl, propyl, isopropyl, butyl, isobutyl, tert-butyl, and phenyl, each group being optionally substituted with 1, 2 or 3 substituents each independently selected from fluoro or C$_{1-4}$alkyl; preferably R$^2$, R$^3$ and R$^4$ are each independently selected from the group comprising methyl, ethyl, propyl, isopropyl, or tert-butyl, and phenyl, each group being optionally substituted with 1, 2 or 3 substituents each independently selected from fluoro or C$_{1-2}$alkyl;

R$^5$ is a group selected from C$_{1-6}$alkyl or phenyl, each group being optionally substituted by one or more substituents independently selected from fluoro or C$_{1-4}$alkyl; preferably R$^5$ is selected from the group comprising methyl, ethyl, propyl, isopropyl, butyl, isobutyl, tert-butyl, and phenyl, each group being optionally substituted with 1, 2 or 3 substituents each independently selected from fluoro or C$_{1-4}$alkyl; preferably R$^5$ is selected from the group comprising methyl, ethyl, propyl, isopropyl, or tert-butyl, and phenyl, each group being optionally substituted with 1, 2 or 3 substituents each independently selected from fluoro or C$_{1-2}$alkyl;

R$^6$ and R$^7$ are each independently hydrogen or a group selected from C$_{1-6}$alkyl or phenyl, each group being optionally substituted by one or more substituents independently selected from fluoro or C$_{1-4}$alkyl; preferably R$^6$ and R$^7$ are each independently hydrogen or are selected from the group comprising methyl, ethyl, propyl, isopropyl, butyl, isobutyl, tert-butyl, and phenyl, each group being optionally substituted with 1, 2 or 3 substituents each independently selected from fluoro or C$_{1-4}$alkyl; preferably R$^6$ and R$^7$ are each independently hydrogen or a group selected from methyl, ethyl, propyl, isopropyl, or tert-butyl, and phenyl, each group being optionally substituted with 1, 2 or 3 substituents each independently selected from fluoro or C$_{1-2}$alkyl;

said process also comprises the steps of:

b) reacting the compound of formula (III) in the presence of at least one oxidizing agent selected from permanganate salt, osmium oxide, hydrogen peroxide, or iodine and silver acetate to produce compound of formula (IV); preferably said oxidizing agent is potassium permanganate; and (IV)

c) deprotecting the compound of formula (IV) to produce compound of formula (I).

In an embodiment, P$^1$ is R$^2$Si(R$^3$)(R$^4$)—. Preferably P$^1$ is selected from the group comprising tert-butyl-dimethyl-silyl, diphenyl-methyl-silyl, dimethyl-phenyl-silyl, trimethyl-silyl, triethyl-silyl and triisopropyl-silyl, each group being optionally substituted by one or more substituents independently selected from fluoro or C$_{1-4}$alkyl; more preferably P$^1$ is tert-butyl-dimethyl-silyl.

According to the invention, step (a) comprises reacting a compound of formula (II), with an acylating or a silylating agent to produce a compound of formula (III), In an embodiment, compound of formula (II) can be reacted with a silylating agent and P$^2$ is R$^2$Si(R$^3$)(R$^4$)—. Preferably P$^2$ is selected from the group comprising tert-butyl-dimethyl-silyl, diphenyl-methyl-silyl, dimethyl-phenyl-silyl, trimethyl-silyl, triethyl-silyl and triisopropyl-silyl, each group being optionally substituted by one or more substituents independently selected from fluoro or C$_{1-4}$alkyl; more preferably P$^2$ is tert-butyl-dimethyl-silyl.

In an embodiment, P$^1$ and P$^2$ are each independently R$^2$Si(R$^3$)(R$^4$)—.

Non-limiting examples of suitable silylating agent can be selected from the group comprising C$_{1-6}$alkylsilylchloride, C$_{1-6}$alkylsilyltriflate, C$_6$arylsilylchloride, C$_6$arylsilyltriflate, C$_{1-6}$alkylC$_6$arylsilylchloride, and C$_{1-6}$alkylC$_6$arylsilyltriflate, each group being optionally substituted by one or more substituents independently selected from fluoro or C$_{1-4}$alkyl.

For example, formation of protected compound of formula (III) can be performed by reaction of compound of formula (II) with a silylating agent such as tert-butyl dimethylsilylchloride, diphenylmethylsilylchloride, dimethylphenylsilylchloride, trimethylsilylchloride, triethylsilylchloride, or triisopropylsilylchloride, or such as tert-butyl dimethylsilyltriflate, diphenylmethylsilyltriflate, dimethylphenylsilyltriflate, trimethylsilyltriflate, triethylsilyltriflate, or triisopropylsilyltriflate. The reaction can be performed in the presence of a suitable base such as imidazole, 2,6-lutidine, collidine, triethylamine, or 1,8-diazabicyclo[5.4.0]undec-7-ene (DBU). The reaction can be performed at room temperature or under reflux. The reaction can be performed in the presence of a suitable solvent such as dimethylformamide, dichloromethane, or toluene, or a mixture thereof.

In an embodiment, compound of formula (II) can be reacted with an acylating agent and $P^2$ is $(R^6R^5R^7)C$—CO—. Preferably $P^2$ is tertbutyl-CO.

In an embodiment, $P^1$ and $P^2$ are each independently $(R^6R^5R^7)C$—CO—.

Non-limiting examples of suitable acylating agent can be selected from the group comprising

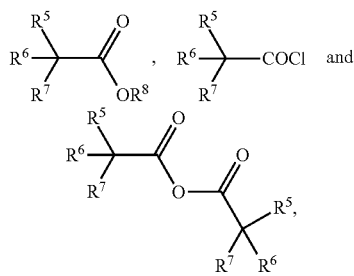

preferably

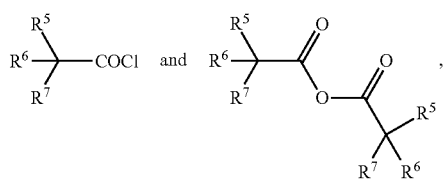

wherein $R^5$, $R^6$, $R^7$ have the same meaning as that defined in claim 1, $R^8$ is a group selected from $C_{1-6}$alkyl, or $C_{2-6}$alkenyl, each group being optionally substituted by one or more substituents independently selected from fluoro or $C_{1-4}$alkyl.

Preferably, the acylating agent can be selected from the group comprising pivaloyl chloride, pivaloyl anhydride and the like.

The acylation when performed with acylating agent such as $C_{2-6}$alkenyl-tert-butyrate, can be performed in the presence of an acid, such as in the presence of sulfuric acid, or in the presence of a $C_{6-10}$arylsulfonic acid, optionally substituted by one or more chloro substituents. Non-limiting examples of a suitable acid include para-toluene sulfonic acid, and sulfuric acid.

The acylation when performed with

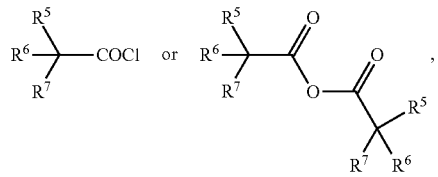

can be performed in the presence of an organic base, such as imidazole, triethylamine and the like.

Step (b) can comprise reacting the compound of formula (III) in the presence of at least one oxidizing agent selected from permanganate salt, osmium oxide, or hydrogen peroxide, or iodine and silver acetate or ruthenium salt to produce compound of formula (IV).

Preferably, step (b) comprises reacting the compound of formula (III) in the presence of at least one oxidizing agent selected from permanganate salt, osmium oxide, or hydrogen peroxide, or iodine and silver acetate to produce compound of formula (IV).

This reaction can be performed in the presence of a co-oxidant such as trimethylamine n-oxide, quinuclidine N-oxide, N-methylmorpholine N-oxide, potassium ferricyanide, tert-butylhydroperoxide, or a phase transfer catalyst such as tetraalkylammonium salts.

Preferably step (b) is performed in the presence of a permanganate salt, such as potassium permanganate. The reaction can be performed in the presence of a suitable acid such as formic acid. The reaction can be performed at low temperature such as temperature below 10° C., preferably below 5° C., preferably around 0° C. The reaction can be performed in the presence of a suitable solvent such as acetone.

According to the invention, step (c) comprises deprotecting the compound of formula (IV) to produce compound of formula (I).

Suitable methods and conditions for deprotecting compound of formula (IV), will be clear to the skilled person and are generally described in the standard handbooks of organic chemistry, such as Greene and Wuts, "*Protective groups in organic synthesis*", 3$^{rd}$ Edition, Wiley and Sons, 1999, which is incorporated herein by reference in its entirety.

For example, when $P^1$ and $P^2$ are each independently $R^2Si(R^3)(R^4)$—, the deprotection can be performed in the presence of a suitable acid, such as hydrochloric acid, acetic acid and the like, or by employing stoichiometric amount of a tetraalkyl ammonium fluoride derivative in a solvent.

For example, when $P^1$ and $P^2$ are each independently $(R^6R^5R^7)C$—CO—, the deprotection can be performed in the presence of a suitable acid, base or reducing agents. Preferably, the deprotection can be performed using a suitable base such as potassium carbonate, for example in methanol.

The compound of formula (II) can be obtained according to method known to the skilled man in the art.

In an embodiment, compound of formula (II) can be prepared by a process comprising the steps of:

i) reacting a compound of formula (V), with an acylating or a silylating agent to produce a compound of formula (VI),

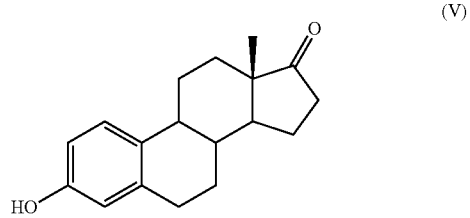

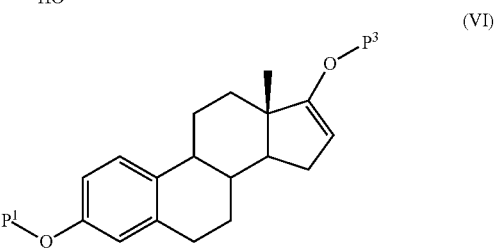

wherein $P^3$ is a protecting group selected from $R^9CO$—, or $R^{10}Si(R^{11})(R^{12})$—, $R^9$ is a group selected from $C_{1-6}$alkyl or $C_{3-6}$cycloalkyl, each group being optionally substituted by one or more substituents independently selected from fluoro or $C_{1-4}$alkyl; preferably $R^9$ is a group selected from $C_{1-6}$alkyl or $C_{3-6}$cycloalkyl, each group being optionally substituted by 1, 2 or 3 substituents independently selected from fluoro or $C_{1-4}$alkyl; preferably $R^9$ is selected from the group comprising methyl, ethyl, propyl, isopropyl, butyl, isobutyl, tert-butyl, cyclopropyl, cyclobutyl, cyclopentyl, or cyclohexyl, each group being optionally substituted by 1, 2 or 3 substituents independently selected from fluoro or $C_{1-4}$alkyl; more preferably $R^9$ is methyl, ethyl, propyl, isopropyl, cyclopentyl, or cyclohexyl, yet more preferably $R^9$ is methyl, or ethyl;

$R^{10}$, $R^{11}$ and $R^{12}$ are each independently a group selected from $C_{1-6}$alkyl or phenyl, each group being optionally substituted by one or more substituents independently selected from fluoro or $C_{1-4}$alkyl; preferably $R^{10}$, $R^{11}$ and $R^{12}$ are each independently a group selected from $C_{1-6}$alkyl or $C_6$aryl, said $C_{1-6}$alkyl or $C_6$aryl, being optionally substituted with 1, 2 or 3 substituents independently selected from fluoro or $C_{1-6}$alkyl; preferably $R^{10}$, $R^{11}$, and $R^{12}$ are each independently selected from the group comprising methyl, ethyl, propyl, isopropyl, butyl, isobutyl, tert-butyl, and phenyl, each group being optionally substituted with 1, 2 or 3 substituents each independently selected from fluoro or $C_{1-4}$alkyl; preferably $R^{10}$, $R^{11}$ and $R^{12}$ are each independently selected from the group comprising methyl, ethyl, propyl, isopropyl, or tert-butyl, and phenyl, each group being optionally substituted with 1, 2 or 3 substituents each independently selected from fluoro or $C_{1-2}$alkyl, ii) reacting the compound of formula (VI) in the presence of palladium acetate or a derivative thereof, or iodine (V) species, to produce compound of formula (VII); and

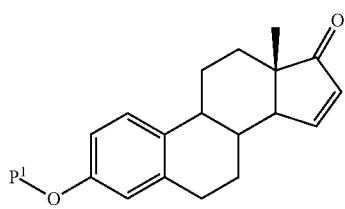

(VII)

iii) reacting the compound of formula (VII) with a reducing agent to produce compound of formula (II).

Preferably, compound of formula (II) can be prepared by a process comprising the steps of:

i) reacting a compound of formula (V), with an acylating or a silylating agent to produce a compound of formula (VI),

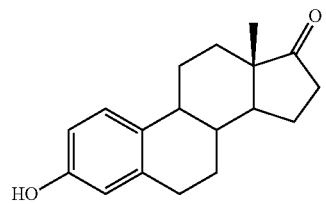

(V)

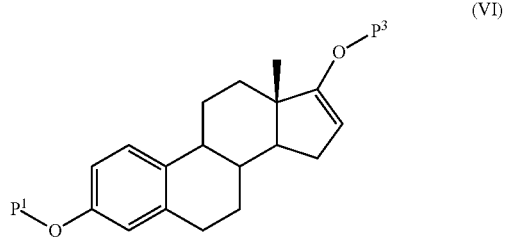

(VI)

wherein $P^3$ is a protecting group selected from $R^9CO$—, or $R^{10}Si(R^{11})(R^{12})$—, $R^9$ is a group selected from $C_{1-6}$alkyl or $C_{3-6}$cycloalkyl, each group being optionally substituted by one or more substituents independently selected from fluoro or $C_{1-4}$alkyl; preferably $R^9$ is a group selected from $C_{1-6}$alkyl or $C_{3-6}$cycloalkyl, each group being optionally substituted by 1, 2 or 3 substituents independently selected from fluoro or $C_{1-4}$alkyl; preferably $R^9$ is selected from the group comprising methyl, ethyl, propyl, isopropyl, butyl, isobutyl, tert-butyl, cyclopropyl, cyclobutyl, cyclopentyl, or cyclohexyl, each group being optionally substituted by 1, 2 or 3 substituents independently selected from fluoro or $C_{1-4}$alkyl; more preferably $R^9$ is methyl, ethyl, propyl, isopropyl, cyclopentyl, or cyclohexyl, yet more preferably $R^9$ is methyl, or ethyl;

$R^{10}$, $R^{11}$ and $R^{12}$ are each independently a group selected from $C_{1-6}$alkyl or phenyl, each group being optionally substituted by one or more substituents independently selected from fluoro or $C_{1-4}$alkyl; preferably $R^{10}$, $R^{11}$ and $R^{12}$ are each independently a group selected from $C_{1-6}$alkyl or $C_6$aryl, said $C_{1-6}$alkyl or $C_6$aryl, being optionally substituted with 1, 2 or 3 substituents independently selected from fluoro or $C_{1-6}$alkyl; preferably $R^{10}$, $R^{11}$ and $R^{12}$ are each independently selected from the group comprising methyl, ethyl, propyl, isopropyl, butyl, isobutyl, tert-butyl, and phenyl, each group being optionally substituted with 1, 2 or 3 substituents each independently selected from fluoro or $C_{1-4}$alkyl; preferably $R^{10}$, $R^{11}$ and $R^{12}$ are each independently selected from the group comprising methyl, ethyl, propyl, isopropyl, or tert-butyl, and phenyl, each group being optionally substituted with 1, 2 or 3 substituents each independently selected from fluoro or $C_{1-2}$alkyl.

ii) reacting the compound of formula (VI) in the presence of palladium acetate or a derivative thereof to produce compound of formula (VII); and

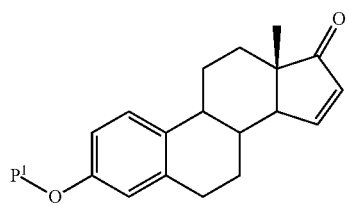

(VII)

iii) reacting the compound of formula (VII) with a reducing agent to produce compound of formula (II).

In an embodiment, $P^1$ is $R^1CO$—; preferably $P^1$ is a group selected from $C_{1-4}$alkylcarbonyl or $C_{4-6}$cycloalkylcarbonyl, each group being optionally substituted by 1, 2 or 3 substituents independently selected from fluoro or $C_{1-4}$alkyl; more preferably $P^1$ is a group selected from $C_{1-2}$alkylcarbonyl or $C_{5-6}$cycloalkylcarbonyl, each group being optionally substituted by 1, 2 or 3 substituents independently selected from fluoro or $C_{1-2}$alkyl; for example $P^1$ is selected from acetyl, tert-butyl-CO—, or cyclohexylcarbonyl, preferably $P^1$ is acetyl.

In an embodiment, $P^3$ is $R^9$CO—; preferably $P^3$ is a group selected from $C_{1-4}$alkylcarbonyl or $C_{4-6}$cycloalkylcarbonyl, each group being optionally substituted by 1, 2 or 3 substituents independently selected from fluoro or $C_{1-4}$alkyl; more preferably $P^3$ is a group selected from $C_{1-2}$alkylcarbony or $C_{5-6}$cycloalkylcarbonyl, each group being optionally substituted by 1, 2 or 3 substituents independently selected from fluoro or $C_{1-4}$alkyl; for example $P^3$ is selected from acetyl, or cyclohexylcarbonyl, preferably $P^3$ is acetyl.

In an embodiment, $P^1$ is $R^1$CO— and $P^3$ is $R^9$CO—. In an another embodiment, $P^1$ is $R^2$Si($R^3$)($R^4$)—. Preferably $P^1$ is selected from the group comprising tert-butyl-dimethyl-silyl, diphenyl-methyl-silyl, dimethyl-phenyl-silyl, trimethyl-silyl, triethyl-silyl and triisopropyl-silyl, each group being optionally substituted by one or more substituents independently selected from fluoro or $C_{1-4}$alkyl; more preferably $P^1$ is tert-butyl-dimethyl-silyl.

In an embodiment, step (i) comprises the steps of (i1) protecting the hydroxyl of compound of formula (V) with a silylating agent to produce a compound of formula (Va), wherein $P^1$ has the same meaning as that defined herein above, preferably wherein $P^1$ is $R^2$Si($R^3$)($R^4$)—; and

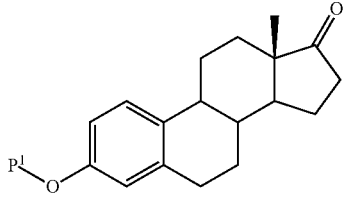

(Va)

(i2) protecting the ketone of compound of formula (Va) in the presence of an acylating agent to produce compound of formula (VI), preferably wherein $P^3$ is $R^9$CO—.

In an embodiment, $P^3$ is $R^{10}$Si($R^{11}$)($R^{12}$)—; preferably $P^3$ is selected from the group comprising tert-butyl-dimethyl-silyl, diphenyl-methyl-silyl, dimethyl-phenyl-silyl, trimethyl-silyl, triethyl-silyl and triisopropyl-silyl, each group being optionally substituted by one or more substituents independently selected from fluoro or $C_{1-4}$alkyl, more preferably $P^3$ is tert-butyl-dimethyl-silyl.

In an embodiment, $P^1$ is $R^2$Si($R^3$)($R^4$)— and $P^3$ is $R^{10}$Si($R^{11}$)($R^{12}$)—.

In another embodiment, $P^1$ is $R^2$Si($R^3$)($R^4$)—; and $P^3$ is $R^9$CO—. Preferably $P^1$ is selected from the group comprising tert-butyl-dimethyl-silyl, diphenyl-methyl-silyl, dimethyl-phenyl-silyl, trimethyl-silyl, triethyl-silyl or triisopropyl-silyl, each group being optionally substituted by one or more substituents independently selected from fluoro or $C_{1-4}$alkyl; more preferably $P^1$ is tert-butyl-dimethyl-silyl; and preferably $P^3$ is a group selected from $C_{1-6}$alkylcarbonyl or $C_{3-6}$cycloalkylcarbonyl, each group being optionally substituted by 1, 2 or 3 substituents independently selected from fluoro or $C_{1-4}$alkyl; preferably $P^3$ is a group selected from $C_{1-4}$alkylcarbonyl or $C_{5-6}$cycloalkylcarbonyl; each group being optionally substituted by 1, 2 or 3 substituents independently selected from fluoro or $C_{1-2}$alkyl; more preferably $P^3$ is $C_{1-2}$alkylcarbony or $C_{5-6}$cycloalkylcarbonyl, for example $P^3$ is acetyl or cyclohexylcarbonyl, preferably acetyl.

Suitable silylating agents and conditions are the same as described herein above for step (a) of the process of the invention.

In an embodiment, wherein $P^1$ is $R^1$CO— and $P^3$ is $R^9$CO—, estrone can be reacted with an acylating agent. Preferably, said acylating agent is $C_{2-6}$alkenyl$C_{1-6}$alkanoate or $C_{2-6}$alkenyl$C_{3-6}$cycloalkanoate. Preferably, the acylating agent is selected from the group comprising $C_{2-6}$alkenylpropanoate, $C_{2-6}$alkenylbutanoate, $C_{2-6}$alkenylpentanoate, $C_{2-6}$alkenylhexanoate, $C_{2-6}$alkenylcyclopropanoate, $C_{2-6}$alkenylcyclobutanoate, $C_{2-6}$alkenylcyclopentanoate, and $C_{2-6}$alkenylcyclohexanoate. More preferably, the acylating agent is selected from the group comprising isopropenyl acetate, isopropenyl propionate, isopropenyl butyrate, isopropenyl isobutyrate, vinyl acetate, vinyl propionate, prop-2-enyl cyclohexanecarboxylate, ethenyl cyclopentanecarboxylate, and vinyl cyclohexanoate. More preferably, the acylating agent is selected from the group comprising isopropenyl acetate, isopropenyl propionate, isopropenyl butyrate, isopropenyl isobutyrate, vinyl acetate, and vinyl propionate. The acylation can be performed in the presence of an acid, such as in the presence of sulfuric acid, or in the presence of an $C_{6-10}$arylsulfonic acid, optionally substituted by one or more chloro substituents. Non-limiting examples of a suitable acid include para-toluene sulfonic acid, and sulfuric acid. For example, estrone of formula (V) can be was reacted with isopropenyl acetate in the presence of sulfuric acid or para-toluene sulfonic acid to give the estra-1,3,5 (10), 16-tetraene-3,17-diol, 3,17-diacetate. The reaction can be performed under reflux, optionally under inert atmosphere, such as nitrogen atmosphere. The product can be used as such in the next step or further purified by known techniques in the art such as by chromatography, for example on silica with a suitable eluant such as methylene chloride/hexane or ethyl acetate/hexane.

In an embodiment, wherein $P^1$ is $R^2$Si($R^3$)($R^4$)— and $P^3$ is $R^{10}$Si($R^{11}$)($R^{12}$)—, estrone of formula (V) can be reacted with a silylating agent. The silylating agent can be selected from the group comprising $C_{1-6}$alkylsilyl triflate, $C_6$arylsilyltriflate, $C_{1-6}$alkyl$C_6$arylsilyltriflate, each group being optionally substituted by one or more substituents independently selected from fluoro or $C_{1-4}$alkyl. For example, formation of protected estrone silyl ether can be performed by reaction of a silylating agent such as tert-butyl dimethylsilyltriflate, diphenylmethylsilyltriflate, dimethylphenylsilyltriflate, trimethylsilyltriflate, triethylsilyltriflate, or triisopropylsilyltriflate. The reaction can be performed in the presence of a suitable base such as imidazole, 2,6-lutidine, collidine, triethylamine, or 1,8-diazabicyclo[5.4.0]undec-7-ene (DBU). The reaction can be performed at room temperature or under reflux. The reaction can be performed in the presence of a suitable solvent such as dichloromethane, toluene or dimethylformamide or a mixture thereof.

Step (ii) of the process for preparing compound of formula (II) comprises reacting the compound of formula (VI) in the presence of palladium acetate or a derivative thereof such as palladium chloride to produce a compound of formula (VII).

In an embodiment, said palladium acetate can be present in stoichiometric amounts, or sub-stoichiometric catalytic amounts. For example the reaction of step (ii) can be performed using stoichiometric amounts of palladium acetate, preferably in a suitable solvent such benzonitrile. This reaction can be performed at room temperature.

In another example, said step (ii) can be performed using sub-stoichiometric catalytic amounts of palladium acetate in the presence of a $C_{1-6}$alkylene carbonate such as allyl carbonate and in the presence of an organotin compound as catalyst.

Preferably, the organotin compound is tri-butyltin methoxide. Preferably the $C_{1-6}$alkylene carbonate is allyl methyl carbonate. The reaction can be performed under reflux conditions, optionally under inert atmosphere such as nitrogen or argon atmosphere.

In another example, said step (ii) can be performed using sub-stoichiometric catalytic amounts of palladium acetate under an oxygen atmosphere.

Alternatively, step (ii) of the process for preparing compound of formula (II) comprises reacting the compound of formula (VI) in the presence of iodine (V) species.

Preferably, said iodine (V) species are selected from o-iodobenzoic acid (IBX also known as 1-hydroxy-1,2-benziodoxal-3(1H)-one-1-oxide) or IBX complexes, such as IBX•N-oxide complexes. Non-limiting examples of suitable IBX complexes include IBX-4-methoxypyridine-N-oxide complex (IBX•MPO complex), and complexes as described in Nicolaou et al. Angew. Chem. Int. Ed. 2002, 41, 996-1000 and Angew. Chem. Int. Ed. 2002, 41, 993-995 hereby incorporated by reference in their entirety.

In another, more preferred embodiment, the iodine (V) species are selected from $HIO_3$ or/and its anhydride $I_2O_5$. These iodine (V) species have the advantage of being mild, safe and chemoselective reagents available at reasonable cost for industrial applications.

Preferably, the oxidation with the iodine (V) species is carried out in the presence of a ligand such as tetrahydrofuran (THF), dimethylsulfoxide (DMSO) or N-oxide derivatives such as N-methylmorpholine-N-oxide, 4-methoxypyridine-N-oxide, trimethylamine-N-oxide.

Preferably, the reaction is performed in the presence of a solvent, such as DMSO. In an embodiment the reaction is kept at 45-65° C. Preferably the reaction is performed at a temperature ranging from 45 to 65° C. in the presence of DMSO.

The next step (iii) in the process comprises the reduction of the compound of formula (IV) with a reducing agent to produce compound of formula (II). Preferably, said reducing agent is a metal hydride compound. For example, the metal hydride compound can be selected from the group comprising $LiAlH_4$, $NaBH_4$, $NaBH(OAc)_3$, $ZnBH_4$, and $NaBH_4/CeCl_3$. preferably, said reducing agent is $NaBH_4/CeCl_3$. For example said reduction can be performed in a suitable solvent or a mixture thereof, such as in tetrahydrofuran, or a mixture of methanol and tetrahydrofuran. The reaction can be performed at low temperatures such as below 15° C., for example below 10° C.

In an embodiment, compound of formula (VII) is not isolated but directly reduced to the alcohol using said reducing agent. In this embodiment, step (ii) and (iii) are performed in one pot. This one-pot/two-step procedure is the shortest chemical pathway described to obtain compound of formula (II).

According to another embodiment, step (i) can be performed in two steps and comprises the steps of (i1) protecting the hydroxyl of compound of formula (V) using a silylating agent to produce a compound of formula (Va), wherein $P^1$ is $R^2Si(R^3)(R^4)$—; and

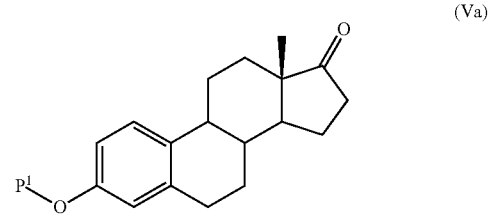

(i2) converting the ketone of compound of formula (Va) to its enol ether in the presence of an acylating agent to produce a compound of formula (VI).

In this embodiment, wherein $P^1$ independently $R^2Si(R^3)(R^4)$—, and $P^3$ is $R^9$—CO—, estrone of formula (V) is reacted with a silylating agent to produce compound of formula (Va). The silylating agent can be selected from the group comprising $C_{1-6}$alkylsilyl chloride, $C_6$arylsilyl chloride, $C_{1-6}$alkyl$C_6$arylsilyl chloride; each group being optionally substituted by one or more substituents independently selected from fluoro or $C_{1-4}$alkyl. For example, formation of protected estrone silyl ether can be performed by reaction of a silylating agent such as tert-butyl dimethylsilylchloride, diphenylmethylsilylchloride, dimethylphenylsilylchloride, trimethylsilylchloride, triethylsilylchloride, or triisopropylsilylchloride. The reaction can be performed in the presence of a base such as imidazole, 2,6-lutidine, collidine, triethylamine, or 1,8-diazabicyclo[5.4.0]undec-7-ene (DBU).

The next step comprises, converting the ketone of compound of formula (Va) in the presence of an acylating agent to produce a compound of formula (VI) wherein $P^3$ is acyl. Suitable acylating agents and conditions are as described herein above. The next step can comprise reacting the formula (VI) wherein $P^3$ is acyl in the presence of palladium acetate or a derivative thereof to produce compound of formula (VII) wherein $P^1$ is $R^2Si(R^3)(R^4)$—. This reaction can be performed as described herein above. The next step in the process comprises the reduction of the compound of formula (VII) with a reducing agent to produce compound of formula (II) wherein $P^1$ is $R^2Si(R^3)(R^4)$—. This reaction can be performed as described herein above.

In another embodiment, compound of formula (II) can be prepared by a process comprising the steps of:

1) reacting a compound of formula (V) with a silylating or an acylating agent to produce compound of formula (Va), wherein $P^1$ has the same meaning as in claim 1;

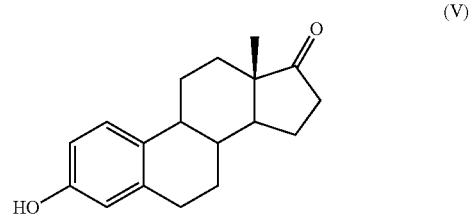

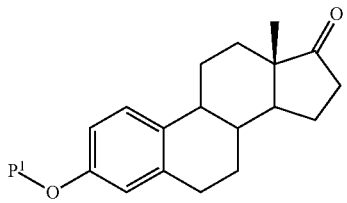

(Va)

2) halogenation or sulfinylation of the compound of formula (Va) to produce a compound of formula (Vb);

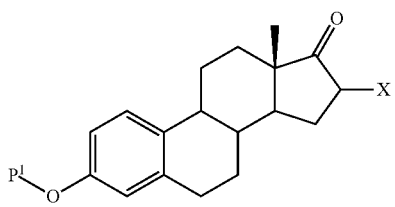

(Vb)

wherein X is halo, or —SO—$R^{20}$, and $R^{20}$ is a group selected from $C_{6-10}$aryl or heteroaryl, each group being optionally substituted by one or more substituents independently selected from chloro or $C_{1-4}$alkyl;

3) dehalogenation or desulfinylation of the compound of formula (Vb) to produce compound of formula (V); and

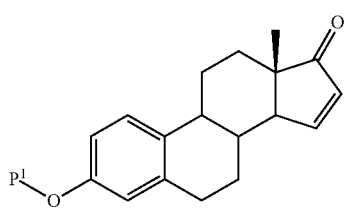

(VII)

4) reacting the compound of formula (VII) with a reducing agent to produce compound of formula (II).

According to step (1) of this embodiment, the hydroxyl of estrone of formula (V) is protected, to produce compound of formula (Va). In an embodiment, estrone of formula (V) can reacted with a silylating agent. Non-limiting examples of suitable silylating agents and conditions are the same as described herein above for step (a) of the process of the invention. For example, formation of protected estrone silyl ether can be performed by reaction of a silylating agent such as tert-butyl dimethylsilylchloride, diphenylmethylsilylchloride, dimethylphenylsilylchloride, trimethylsilylchloride, triethylsilylchloride, or triisopropylsilylchloride, or such as tert-butyl dimethylsilyltriflate, diphenylmethylsilyltriflate, dimethylphenylsilyltriflate, trimethylsilyltriflate, triethylsilyltriflate, or triisopropylsilyltriflate. The reaction can be performed in the presence of a suitable base such as imidazole, 2,6-lutidine, collidine, triethylamine, or 1,8-diazabicyclo[5.4.0]undec-7-ene (DBU). The reaction can be performed at room temperature or under reflux. The reaction can be performed in the presence of a suitable solvent such as dichloromethane, toluene, or dimethylformamide or a mixture thereof.

In another embodiment, estrone of formula (V) can be reacted with an acylating agent. In an embodiment, said acylating agent can be selected from the group comprising $C_{2-6}$alkenyl$C_{1-6}$alkanoate, $C_{2-6}$alkenyl$C_{3-6}$cycloalkanoate, acyl chloride, and anhydrides. Preferably, the acylating agent is selected from the group comprising $C_{2-6}$alkenylpropanoate, $C_{2-6}$alkenylbutanoate, $C_{2-6}$alkenylpentanoate, $C_{2-6}$alkenylhexanoate, $C_{2-6}$alkenylcyclopropanoate, $C_{2-6}$alkenylcyclobutanoate, $C_{2-6}$alkenylcyclopentanoate, and $C_{2-6}$alkenylcyclohexanoate, acyl chloride and anhydrides. More preferably, the acylating agent is selected from the group comprising isopropenyl acetate, isopropenyl propionate, isopropenyl butyrate, isopropenyl isobutyrate, vinyl acetate, vinyl propionate, prop-2-enyl cyclohexanecarboxylate, ethenyl cyclopentanecarboxylate, vinyl cyclohexanoate, acetyl chloride, propionylchloride, butyrylchloride, acetic anhydride and the like. More preferably, the acylating agent is selected from the group comprising isopropenyl acetate, isopropenyl propionate, isopropenyl butyrate, isopropenyl isobutyrate, vinyl acetate, vinyl propionate, acetyl chloride, propionylchloride, butyrylchloride, acetic anhydride and the like. The acylation when performed with $C_{2-6}$alkenyl$C_{1-6}$alkanoate or $C_{2-6}$alkenyl$C_{3-6}$cycloalkanoate, can be performed in the presence of an acid, such as in the presence of sulfuric acid, or in the presence of a $C_{6-10}$arylsulfonic acid, optionally substituted by one or more chloro substituents. Non-limiting examples of a suitable acid include para-toluene sulfonic acid, and sulfuric acid. The acylation when performed with an acyl chloride or an anhydride, can be performed in the presence of an organic base, such as imidazole, triethylamine and the like.

Step (2) of the process comprises halogenation or sulfinylation of the compound of formula (Va) to produce a compound of formula (Vb); wherein X is halo, or —SO—$R^{20}$, and $R^{20}$ is a group selected from $C_{6-10}$aryl or heteroaryl, each group being optionally substituted by one or more substituents independently selected from chloro or $C_{1-4}$alkyl; preferably $R^{20}$ is phenyl or pyridinyl.

In an embodiment, step (2) is a halogenation and the halogenation is performed by reacting the compound of formula (Va) with a halogenating reagent. Preferably, step 2) is a bromination, and X is bromo. In an embodiment, the brominating reagent can be selected from the group comprising copper(II) bromide, bromine, pyridine bromine perbromine and the like.

In another embodiment, step (2) is a sulfinylation and the sulfinylation is performed by reacting the compound of formula (Va) with a base and with a sulfinylation reagent. Non-limiting examples of sulfinylation reagent include methyl 2-pyridinesulfinate, methyl benzenesulfinate, methyl 4-methyl-benzenesufinate, and methyl 4-chloro-benzene sulfinate. The base used in the sulfinylation step can be selected from the group comprising potassium hydride, potassium terbutylate, sodium hydride, sodium terbutylate and a mixture thereof. Non-limiting examples of suitable experimental conditions for the sulfinylation are described in Barry M Trost et al in Journal of Organic Chemistry, 1993, 58, 1579-81; hereby incorporated by reference.

The next step (3) comprises the dehalogenation or desulfinylation of the compound of formula (Vb) to produce compound of formula (V).

In an embodiment, step (2) is a halogenation, and step (3) comprises a dehalogenation step which can be performed in the presence of a base. The base can be selected from the group comprising imidazole, collidine, 2,6-lutidine, triethylamine, or 1,8-diazabicyclo[5.4.0]undec-7-ene (DBU). The dehalogenation reaction can be performed at a temperature between 30° C. and 130° C. Preferably, the dehalogenation reaction is performed in an aprotic solvent.

In another embodiment, step (2) is a sulfinylation, and step (3) comprises a desulfinylation which can be carried out with heat optionally in the presence of cupric sulfate. The temperature of the desulfinylation step can be between 80° C. and 130° C., preferably between 90° C. and 120° C., preferably between 100° C. and 115° C.

The next step (4) in the process comprises the reduction of the compound of formula (Vb) with a reducing agent to produce compound of formula (II). Preferably, said reducing agent is a metal hydride compound. For example, the metal hydride compound can be selected from the group comprising $LiAlH_4$, $NaBH_4$, $NaBH(OAc)_3$, $ZnBH_4$, and $NaBH_4/CeCl_3$. Preferably, said reducing agent is $NaBH_4/CeCl_3$. For example said reduction can be performed in a suitable solvent or a mixture thereof, such as in tetrahydrofuran, or a mixture of methanol and tetrahydrofuran. The reaction can be performed at low temperatures such as below 15° C., for example below 10° C.

The present process for preparing compound (I) allows the preparation of estra-1,3,5(10)-triene-3,15α,16α,17β-tetrol (sterol) as the major product with little or no estra-1,3,5(10)-triene-3,15β,16β,17β-tetrol isomer being formed. As used herein little refers to obtaining more than 90% of estetrol and less than 10% of the 15β,16β,17β-tetrol isomer, preferably less than 5% of the 15β,16β,17β-tetrol isomer, more preferably less than 1% of the 15β,16β,17β-tetrol isomer.

The process according to the invention has the advantage that estetrol, can be obtained in a reduced number of steps compared to prior art processes, which is more convenient for an economical and industrial synthesis.

The present invention also encompasses the use of estetrol directly obtained by the process the invention for the manufacture of a pharmaceutical composition, preferably for use in a method selected from a method of hormone replacement therapy, a method of treating vaginal dryness, a method of contraception, a method of enhancing libido, of method of treating skin, a method of promoting wound healing, and a method of treating or preventing a disorder selected from the group consisting of autoimmune diseases, breast tumors and colorectal tumors.

The invention is illustrated but not limited by the following examples.

EXAMPLES

Example 1

Preparation of a Compound of Formula (I) Using tert-butyl-dimethyl-silyl Group as Protecting Group for $P^1$ and $P^2$ According to an Embodiment of the Invention Step 1: estra-1,3,5(10),15-tetraene-3,17β-diol bis(dimethyl-tert-butylsilyl) ether The starting material 3-t-butyldimethylsiloxy-estra-1,3,5 (10)-15-tetraene-17β-ol can be prepared as described in Example 3 and 4. To a solution of 3-t-butyldimethylsiloxy-estra-1,3,5 (10)-15-tetraene-17β-ol (10 g, 0.025 mole) in 100 ml of dimethylformamide were added imidazole (4.4 g, 0.065 mole) and dimethyl-tert-butylsilyl-chloride (1.5 eq.) and allowed to stand at room temperature for 6 hours. The resulting solution was diluted with ethyl acetate, washed with water and evaporated. The residue was crystallized from methanol to afford (10 g) of estra-1,3,5(10),15-tetraene-3,17β-diol bis (dimethyl-tert-butylsilyl) ether.

NMR ($CDCl_3$): 0.08 (6H, s, 17-OSi($CH_3$)$_2$, 0.18 (6H, 3-OSi($CH_3$)$_2$, 0.81 (3H, s, 18-$CH_3$), 0.91 (9H, 17-OSi-t-Bu), 0.97 (9H, s, 3-OSi-t, Bu), 4.33 (1H, broad s, 17 aH), 5.60 (1H, m, 15-H, 5.95 (1H, broad, d, 16H), 6.45-6.75 (2H, 2- and 4H), 7.12 (1H, d, J=8 Hz, 1H).
mp: 89-91° C.

Step 2: estra-1,3,5(10),15α,16α,17β-tetrol

To a stirred solution of estra-1,3,5(10),15-tetraene-3,17β-diol bis(dimethyl-tert-butylsilyl) ether (10 g, 0.02 mole) and formic acid (0.06 mole, 2.3 ml) in acetone (100 ml) at 0° C. was added gradually a solution of potassium permanganate (3.15 g, 0.02 mole) in water (20 ml) and acetone (100 ml). After completion of the reaction, the reaction was quenched with a 10% aqueous solution of $KHSO_3$. Acetone was partially removed and extracted with ethyl acetate, an washed with water. Ethyl acetate was concentrated under reduced pressure and diluted with heptane. The precipitate was collected by filtration and dissolved in acetone (100 ml). To the solution 5N hydrochloric acid (20 ml) was added. After completion of the reaction the resulting solution was diluted with water. The solid was collected by filtration, washed with heptane and crystallized from a mixture of methanol and water to afford the title compound.

Example 2

Preparation of a Compound of Formula (I) Using tert-butyl-dimethyl-silyl Group as Protecting Group for $P^1$ and pivaloyl for $P^2$ According to an Embodiment of the Invention The starting material 3-t-butyldimethylsiloxy-estra-1,3,5 (10)-15-tetraene-17β-ol can be prepared as described in Example 3 and 4. To a solution of 3-tert-butyldimethylsilyloxy-estra-1,3,5(10)-15-tetraene-17-ol (30 g, 0.078 mole) in 300 ml of dichloromethane and 11 ml of triethylamine were added drop wise 10.36 g (0.086 mole) of pivaloyl chloride in 50 ml of methylene chloride at 0° C. At the end of the addition the solution was stirred at room temperature for 1 hour. Water was added and the organic layer was washed two time with 100 ml of water. Heptane was added and the product was collected by filtration and used in the next step without any other purification.

3-tertbutyl-dimethylsilyloxy-estra-1,3,5(10)-15-tetraene-17β-pivaloate was converted to its 15α,16α derivative following the procedure described in example 1 step 2.

Then this 3-terbutyl-dimethylsilyloxy-estra-1,3,5(10)-15α,16α-diol-triene-17β-pivaloate (10 g, 0.02 mole) and $K_2CO_3$ (2.76 g, 0.02 mole) was suspended in methanol 200 ml and stirred for 4 hours at room temperature. Water 300 ml was added and the mixture was neutralized with 0.1N HCl. The product was collected by filtration and dried to afford 7.5 g (90% yield) of 3-terbutyl-dimethylsilyloxy-estra-1,3,5 (10)-triene-15α,16α,17β-triol.

Deprotection in acidic medium of the silyl protecting group was performed using the same conditions as described in example 1 step 2, and allowed this compound to be converted to estetrol in 90% yield

Example 3

Preparation of a Compound of Formula (II) Wherein $P^1$ is t-butyldimethylsilyl According to an Embodiment of the Invention Step 1: 3,17-di-t-butyldimethylsiloxy-estra-1,3,5 (10)-16-tetraene-17-ol To a solution of estrone (50 g, 0.185 mole) and 2,6-lutidine (62 g, 0.58 mole) in dichloromethane 400 ml was added drop wise t-butyl-dimethylsilyl-triflate (102.6 g, 0.39 mole). The solution was stirred at room temperature for 6 hours. Water (300 ml) was added and the organic layer was washed with a diluted solution of sodium carbonate. The dichloromethane solution was partially evaporated and ethyl acetate was added. Diisopropyl ether was added to this solution. The mixture was stirred for 2 hours at 0° C. The precipitate was collected by filtration and dried. 83 g of the title compound were obtained (90% yield).

Step 2: 3-t-butyldimethylsiloxy-estra-1,3,5(10)-15-tetraene-17-one

To a solution of 3,17-di-t-butyldimethylsiloxy-estra-1,3,5 (10)-16-tetraene-17-ol 83 g (0.166 mole) in 400 ml of acetonitrile was added Pd(OAc)$_2$ 3.8 g (0.017 mole) in an oxygen atmosphere. The mixture was stirred at 40° C. for 12 hours then filtered through a pad of celite. A diluted solution of sodium carbonate was added and the mixture was extracted with ethyl acetate.

After concentration, diisopropyl ether was added and the mixture was stirred at 0° C. for one hour. The product (54.7 g, 86% yield) was collected by filtration and used in the next step without further purification.

Step 3: 3-t-butyldimethylsiloxy-estra-1,3,5(10)-15-tetraene-17-ol

The collected material (54.7 g, 0.143 mole) was dissolved in THF 300 ml and a solution of cerium chloride heptahydrate (53.3 g, 0.143 mole) in methanol (300 ml) was added. The mixture was cooled to 0° C. Sodium borohydride (8.12 g, 0.213 mole, 1.5 eq) was added portion wise keeping the temperature below 9° C. At this end of the addition the mixture was stored for one hour then quenched by addition of a 2N HCl solution (100 ml). The solution was partly evaporated in situ and water (4 L) was added. The precipitate was collected by filtration and dried. After crystallization from a mixture of ethanol/diisopropyl ether the product was collected by filtration and dried. It weighed 46.6 g (85% yield).

Example 4

Preparation of a Compound of Formula (II) Wherein P$^1$ is t-butyldimethylsilyl According to an Embodiment of the Invention Step 1: 3-t-butyldimethylsiloxy-estra-1,3,5(10)-triene-17-one To a solution of estrone (100 g, 0.37 mole) in 400 ml of dichloromethane, imidazole (50.36 g, 0.74 mole) and t-butyl-dimethylsilyl chloride (61.3 g, 0.41 mole) were added. The solution was stirred at room temperature for 24 hours. Then water (200 ml) was added. The organic layer was partially evaporated and diisopropyl ether added. The white solid formed was collected by filtration and dried. It weighed 135.2 g, yield 95%, mp 172° C.

1H NMR (200 MHz): 7.12 (d, J=7.9 Hz, 1H), 6.61 (m, 2H), 2.84 (m, 3H), 2.06-1.45 (m, 12H), 0.97 (s, 9H), 0.91 (s, 3H), 0.18 (s, 6H).

Step 2: 3-t-butyldimethylsiloxy-estra-1,3,5(10)-16-tetraene-17-acetate 3-t-butyldimethylsiloxy-estra-1,3,5(10)-triene-17 one 135 g (0.351 mole) were poured in 600 ml of isopropenyl acetate and 12 g of para-toluene-sulfonic acid. The mixture was refluxed. Acetone and isopropenyl acetate were continuously distilled off until the internal temperature reached 98° C. Then the mixture was cooled to 0° C. and potassium carbonate added. After one hour at 0° C. the mixture was filtered. The resulting solution was partially concentrated and diisopropyl ether added. The precipitate was collected by filtration and crystallized from a mixture of ethyl acetate and heptane. The product was collected by filtration and dried. It weighed 119.5 g (yield 80%).

Step 3: 3-t-butyldimethylsiloxy-estra-1,3,5 (10)-15-tetraene-17-ol

To a solution of 3-t-butyldimethylsiloxy-estra-1,3,5(10)-16-tetraene-17-acetate 119.5 g (0.280 mole) in acetonitrile (1500 ml) were added 27.2 g (0.085 mole of tributyltin methoxide, 11.2 g (0.05 mole) of palladium acetate and 64 ml (0.560 mole) of allyl methyl carbonate. The mixture was refluxed for 2 hours then cooled to room temperature and filtered through a pad of silica gel. The mixture was diluted with water and extracted with ethyl acetate. After concentration to one third of the initial volume diisopropyl ether was added and the solution cooled at 0° C. for one hour.

The product was collected by filtration. It weighed 91 g (85% yield) and was used in the next step without further purification.

Step 4: 3-t-butyldimethylsiloxy-estra-1,3,5(10)-15-tetraene-17-ol

The reduction step was performed as described in step 3 of example 2: the collected material was dissolved in THF and a solution of cerium chloride heptahydrate (1 eq) in methanol was added. The mixture was cooled to 0° C. sodium borohydride (1.5 eq) was added portion wise keeping the temperature below 9° C. At this end of the addition the mixture was stored for one hour then quenched by addition of a 2N HCl solution. The solution was partly evaporated in situ and water was added. The precipitate was collected by filtration and dried. After crystallization from a mixture of ethanol/diisopropyl ether the product was collected by filtration and dried.

Example 5

Preparation of a Compound of Formula (II) Wherein P$^1$ is tert-butyldimethylsilyl According to an Embodiment of the Invention Step 1: 3-tert-butyldimethylsilyloxy-estra-1,3,5(10)-triene-17-one To a solution of 3-hydroxy-estra-1,3,5(10)-triene-17-one (100 g, 0.370 mole) in 500 ml of dichloromethane was added tert-butyldimethylsilyl-chloride (58.3 g, 0.388 mole) and imidazole (26.4 g, 0.388 mole). The mixture was stirred for 24 hours at room temperature. Water (300 ml) was added and the organic layer was washed with 200 ml of water. After concentration the product was crystallized from a mixture of ethanol/diisopropyl ether, collected by filtration and dried. It weighed 145 g (95% yield).

Step 2: 3-tert-butyldimethylsilyloxy-estra-1,3,5(10)-15-tetraene-17-one

A solution of potassium terbutylate (50 g, 0.45 mole) in 800 ml of tetrahydrofuran was treated with 3-tert-butyldimethylsilyloxy-estra-1,3,5(10)-triene-17-one (86.5 g, 0.225 mole) under nitrogen and stirred for 1 hour, then methyl benzenesulfinate (70.2 g, 0.45 mole) and triethylamine were added. After stirring for 2 hours the solution was poured in 1000 ml of water and 70 ml of hydrochloric acid keeping the temperature below 5° C. 1000 ml of toluene was added, phases are separated and the solution was heated to distil off the solvent until the temperature reached 115° C. Reflux was maintained for 5 hours.

Toluene was washed with two time water, and then partially concentrated. Heptane was added. After one hour at 5° C. the solid was collected by filtration and used in the reduction step without further purification.

Step 3: 3-tert-butyldimethylsilyloxy-estra-1,3,5(10)-15-tetraene-17-ol

The material collected in step 2 was dissolved in THF 300 ml and a solution of cerium chloride heptahydrate (123 g, 0.33 mole) in methanol (300 ml) was added. The mixture was cooled to 0° C. and sodium borohybride (17.8 g, 0.47 mole, 1.5 q) was added portionwise keeping the temperature below 9° C. At this end of the addition the mixture was stirred for one hour then quenched by addition of a 2N HCl solution (100 ml), extracted with ethyl acetate and washed with water. The organic layer was partly evaporated then diisopropylether was added. The precipitate was collected by filtration and dried. After crystallization form a mixture of ethanol/diisopropyl ether the title compound was isolated in 90% yield as an off white solid.

Example 6

Preparation of a Compound of Formula (II) Wherein $P^1$ is tert-butyldimethylsilyl According to an Embodiment of the Invention Step 1: 3-tert-butyldimethylsilyloxy-estra-1,3,5(10)-triene-17-one 3-tert-butyldimethylsilyloxy-estra-1,3,5(10)-triene-17-one was prepared as described in step 1 of Example 5.

Step 2: 3-tert-butyldimethylsilyloxy-estra-1,3,5(10)-15-tetraene-17-one (via X=Br)

Copper(II) bromide (100 g, 0.45 mole) was added to a warm solution of 3-tert-butyldimethylsilyloxy-estra-1,3,5(10)-triene-17-one (86.4 g, 0.225 mole) in methanol (500 ml) and the mixture was heated under reflux for 2 hours. The hot mixture was filtered and was poured in a mixture of dichloromethane (1000 ml) and water (800 ml). The organic layer was washed with water.

To this solution imidazole (18.3 g, 0.27 mole) was added and heated under reflux for 6 hours. After cooling water (500 ml) was added and the organic layer was concentrated. The residue was crystallized from a mixture of ethyl acetate and heptane.

Step 3: 3-tert-butyldimethylsilyloxy-estra-1,3,5(10)-15-tetraene-17-ol

The reduction step was performed as described in step 3 of example 1: The material collected in step 2 of example 2 was dissolved in THF and a solution of cerium chloride heptahydrate (about 1 eq) in methanol was added. The mixture was cooled to 0° C. and sodium borohybride (1.5 eq) was added portionwise keeping the temperature below 9° C. At this end of the addition the mixture was stirred for one hour then quenched by addition of a 2N HCl solution, extracted with ethyl acetate and washed with water. The organic layer was partly evaporated then diisopropylether was added. The precipitate was collected by filtration and dried. After crystallization form a mixture of ethanol/diisopropyl ether the title compound was isolated as an off white solid.

Example 7

Preparation of a Compound of Formula (II) Wherein $P^1$ is tert-butyldimethylsilyl According to an Embodiment of the Invention Step 1: 3-tert-butyldimethylsilyloxy-estra-1,3,5(10)-triene-17-one 3-tert-butyldimethylsilyloxy-estra-1,3,5(10)-triene-17-one was prepared as described in step 1 of Example 5.

Step 2: 3-tert-butyldimethylsilyloxy-estra-1,3,5(10)-15-tetraene-17-one (via X=pyridinesulfinic)

3-tert-butyldimethylsilyloxy-estra-1,3,5(10)-triene 17-one (8.64 g, 0.0225 mole) was added to a suspension of potassium hydride (3 eq. 35% dispersion in oil) in tetrahydrofuran 100 ml. methyl 2-pyridinesulfinate (5.3 g, 0.034 mole, 1.5 eq) was added. After 30 min at room temperature the reaction was poured into a sulfate buffer. The aqueous phase was neutralized by an aqueous solution of sodium carbonate then extracted with toluene. The solution was heated to 110° C. for one hour. After cooling to room temperature the solution was washed with a diluted solution of sodium hydroxide then with water. The organic layer was partly concentrated following by an addition of heptane. The 3-tert-butyldimethylsilyloxy-estra-1,3,5(10)-15-tetraene-17-one was collected by filtration.

Step 3: 3-tert-butyldimethylsilyloxy-estra-1,3,5(10)-15-tetraene-17-ol

The reduction step was performed as described in step 3 of example 1: The material collected in step 2 of example 3 was dissolved in THF and a solution of cerium chloride heptahydrate in methanol was added. The mixture was cooled to 0° C. and sodium borohybride (1.5 eq) was added portionwise keeping the temperature below 9° C. At this end of the addition the mixture was stirred for one hour then quenched by addition of a 2N HCl solution, extracted with ethyl acetate and washed with water. The organic layer was partly evaporated then diisopropylether was added. The precipitate was collected by filtration and dried. After crystallization form a mixture of ethanol/diisopropyl ether the title compound was isolated as an off white solid.

It is to be understood that although preferred embodiments and/or materials have been discussed for providing embodiments according to the present invention, various modifications or changes may be made without departing from the scope and spirit of this invention.

The invention claimed is:

1. A process for the preparation of a compound of formula (I), or a hydrate or solvate thereof;

said process comprising the steps of
a) reacting a compound of formula (II), with a silylating agent to produce a compound of formula (III),

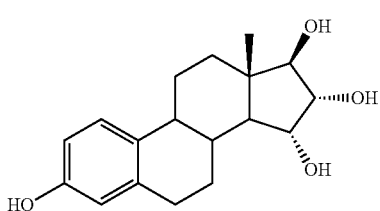
(I)

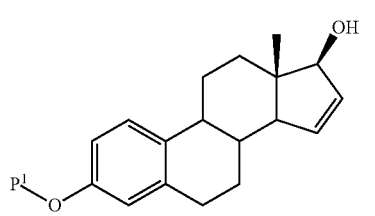
(II)

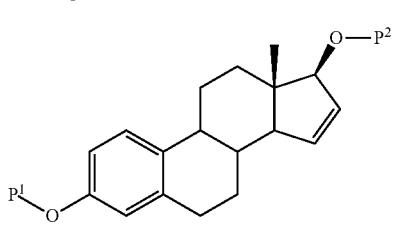
(III)

wherein $P^1$ is a protecting group selected from $R^1CO—$, or $R^2Si(R^3)(R^4)—$, and $P^2$ is $(R^2)Si(R^3)(R^4)—$, wherein $R^1$ is a group selected from $C_{1-6}$alkyl or $C_{3-6}$cycloalkyl, each group being optionally substituted by one or more substituents independently selected from fluoro or $C_{1-4}$alkyl; $R^2$, $R^3$ and $R^4$ are each independently a group selected from $C_{1-6}$alkyl or phenyl, each group being optionally substituted by one or more substituents independently selected from fluoro or $C_{1-4}$alkyl;
b) reacting the compound of formula (III) in the presence of at least one oxidizing agent selected from permanganate salt, osmium oxide, hydrogen peroxide, or iodine and silver acetate to produce a compound of formula (IV); and

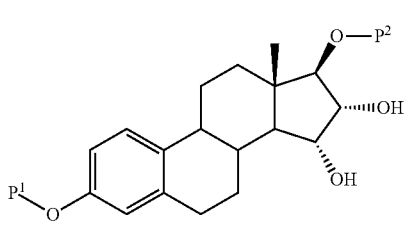
(IV)

c) deprotecting the compound of formula (IV) to produce the compound of formula (I).
2. The process according to claim 1, wherein $P^1$ is $R^2Si(R^3)(R^4)—$, and $P^2$ is $(R^2)Si(R^3)(R^4)—$.
3. The process according to claim 1 or 2, wherein the silylating agent is selected from $C_{1-6}$alkylsilylchloride, $C_{1-6}$alkylsilyltriflate, $C_6$arylsilyl chloride, $C_6$arylsilyltriflate, $C_{1-6}$alkyl$C_6$arylsilylchloride, or $C_{1-6}$alkyl$C_6$arylsilyltriflate, each group being optionally substituted by one or more substituents independently selected from fluoro or $C_{1-4}$alkyl.
4. The process according to claim 1, wherein in step (b) said oxidizing agent is potassium permanganate.
5. The process according to claim 4, wherein step (b) is performed in the presence of an acid.
6. The process according to claim 1, further comprising preparing the compound of formula (II) by a process comprising the steps of:
i) reacting a compound of formula (V), with an acylating agent and/or a silylating agent to produce a compound of formula (VI),

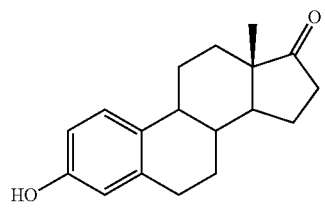
(V)

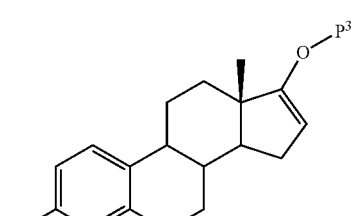
(VI)

wherein $P^3$ is a protecting group selected from $R^9CO—$, or $R^{10}Si(R^{11})(R^{12})—$, wherein $R^9$ is a group selected from $C_{1-6}$alkyl or $C_{3-6}$cycloalkyl, each group being optionally substituted by one or more substituents independently selected from fluoro or $C_{1-4}$alkyl; $R^{10}$, $R^{11}$ and $R^{12}$ are each independently a group selected from $C_{1-6}$alkyl or phenyl, each group being optionally substituted by one or more substituents independently selected from fluoro or $C_{1-4}$alkyl;
ii) reacting the compound of formula (VI) in the presence of palladium acetate or a derivative thereof, or an iodine (V) species, to produce a compound of formula (VII); and

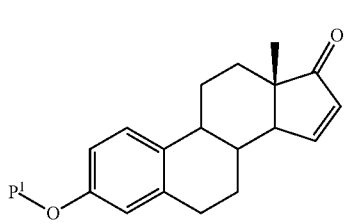
(VII)

iii) reacting the compound of formula (VII) with a reducing agent to produce the compound of formula (II).
7. The process according to claim 6, wherein $P^3$ is $R^9CO—$.
8. The process according to claim 6, wherein step (i) comprises the steps of
(i1) protecting the hydroxyl of the compound of formula (V) with a silylating agent or an acylating agent to produce a compound of formula (Va), wherein $P^1$ has the same meaning as that defined in claim 1; and

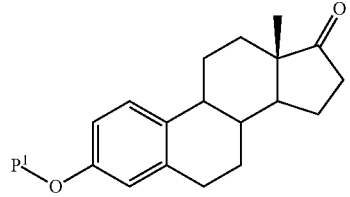
(Va)

(i2) protecting the ketone of the compound of formula (Va) in the presence of an acylating agent to produce compound of formula (VI).

9. The process according to claim 1, further comprising preparing the compound of formula (II) by a process comprising the steps of
1) reacting a compound of formula (V) with a silylating agent or an acylating agent to produce a compound of formula (Va), wherein $P^1$ has the same meaning as in claim 1;

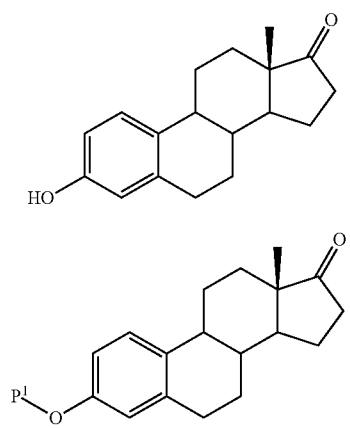
(V)

(Va)

2) performing halogenation or sulfinylation of the compound of formula (Va) to produce a compound of formula (Vb);

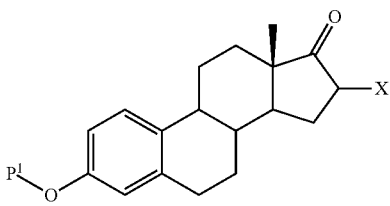
(Vb)

wherein X is halo, or $-SO-R^{20}$, and $R^{20}$ is a group selected from $C_{6-10}$ aryl or heteroaryl, each group being optionally substituted by one or more substituents independently selected from chloro or $C_{1-4}$alkyl;

3) performing dehalogenation or desulfinylation of the compound of formula (Vb) to produce the compound of formula (VII); and

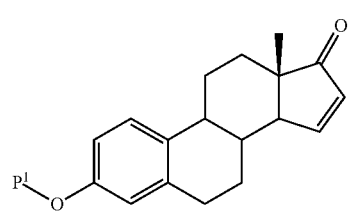
(VII)

4) reacting the compound of formula (VII) with a reducing agent to produce the compound of formula (II).

10. The process according to claim 9, wherein step (2) is performing a sulfinylation, comprising reacting the compound of formula (Va) with a base and with a sulfinylation reagent.

11. The process according to claim 9, wherein step (2) is a performing a halogenation, comprising reacting the compound of formula (Va) with a halogenating reagent.

12. The process according to claim 6 or claim 10, wherein the reducing agent is selected from metal hydride compounds.

13. The process according to claim 6 or claim 10, wherein the silylating agent is selected from $C_{1-6}$alkylsilylchloride, $C_{1-6}$alkylsilyltriflate, $C_6$arylsilylchloride, $C_6$arylsilyltriflate, $C_{1-6}$alkyl$C_6$arylsilylchloride, and $C_{1-6}$alkyl$C_6$arylsilyltriflate, each group being optionally substituted by one or more substituents independently selected from fluoro or $C_{1-4}$alkyl.

14. The process according to claim 6 or claim 10, wherein the acylating agent is selected from $C_{2-6}$alkenyl$C_{1-6}$alkanoates, $C_{2-6}$alkenyl$C_{3-6}$cycloalkanoate, acyl chlorides and anhydrides.

15. The process according to claim 1, wherein in step (b) said oxidizing agent is osmium tetroxide.

* * * * *